United States Patent
Vetter et al.

(10) Patent No.: US 6,936,014 B2
(45) Date of Patent: Aug. 30, 2005

(54) DEVICES AND METHODS FOR PERFORMING PROCEDURES ON A BREAST

(75) Inventors: James W. Vetter, Portola Valley, CA (US); Scott C. Anderson, Sunnyvale, CA (US); Jordan S. Tuttle, Portola Valley, CA (US); Daniel M. Brounstein, Fremont, CA (US)

(73) Assignee: Rubicor Medical, Inc., Redwood City, CA (US)

(*) Notice: Subject to any disclaimer, the term of this patent is extended or adjusted under 35 U.S.C. 154(b) by 0 days.

(21) Appl. No.: 10/272,448

(22) Filed: Oct. 16, 2002

(65) Prior Publication Data

US 2004/0077971 A1 Apr. 22, 2004

(51) Int. Cl.[7] .............................................. A61B 10/00
(52) U.S. Cl. ..................................................... 600/564
(58) Field of Search ................................. 600/564, 567, 600/585, 434; 606/114, 170, 116, 50, 41, 45; 607/101; 128/899

(56) References Cited

U.S. PATENT DOCUMENTS

| | | |
|---|---|---|
| 1,813,902 A | 7/1931 | Bovie |
| 2,816,552 A | 12/1957 | Hoffman |
| 3,320,957 A | 5/1967 | Sokolik |
| 3,732,858 A | 5/1973 | Banko |
| 3,749,085 A | 7/1973 | Willson |
| 3,910,279 A | 10/1975 | Okada et al. |
| 3,955,578 A | 5/1976 | Chamness et al. |
| 4,099,518 A | 7/1978 | Baylis et al. |
| 4,245,653 A | 1/1981 | Weaver |
| 4,347,846 A | 9/1982 | Dormia |
| 4,611,594 A | 9/1986 | Grayhack |
| 4,650,466 A | 3/1987 | Luther |
| 4,890,611 A | 1/1990 | Monfort |
| 4,903,696 A | 2/1990 | Stasz et al. |
| 4,966,604 A | 10/1990 | Reiss |
| 5,071,424 A | 12/1991 | Reger |
| 5,083,570 A | 1/1992 | Mosby |
| 5,100,423 A | 3/1992 | Fearnot |
| 5,147,355 A | 9/1992 | Friedman et al. |
| 5,152,293 A | 10/1992 | Vonesh et al. |
| 5,156,610 A | 10/1992 | Reger |
| 5,174,296 A | 12/1992 | Watanabe et al. |
| 5,176,688 A | 1/1993 | Narayan |
| 5,192,291 A | 3/1993 | Pannek |
| 5,211,651 A | 5/1993 | Reger |
| 5,217,479 A | 6/1993 | Shuler |
| 5,224,488 A | 7/1993 | Neuffer |
| 5,224,945 A | 7/1993 | Pannek et al. |
| 5,282,484 A | 2/1994 | Reger |
| 5,308,321 A | 5/1994 | Castro |
| 5,318,576 A | 6/1994 | Plassche |
| 5,325,860 A | 7/1994 | Seward et al. |
| 5,415,656 A | 5/1995 | Tihon et al. |
| 5,441,510 A | 8/1995 | Simpson et al. |
| 5,527,326 A | 6/1996 | Hermann |
| 5,554,163 A | 9/1996 | Shturman |
| 5,630,426 A | 5/1997 | Eggers et al. |
| 5,632,754 A | 5/1997 | Farley et al. |
| 5,672,172 A | 9/1997 | Zupkas |

(Continued)

FOREIGN PATENT DOCUMENTS

| | | |
|---|---|---|
| DE | 195 28 440 A1 | 2/1997 |
| DE | 197 06 751 A1 | 2/1997 |
| EP | 0 472 368 B1 | 2/1992 |

(Continued)

*Primary Examiner*—Max F. Hindenburg
*Assistant Examiner*—Brian Szmal
(74) *Attorney, Agent, or Firm*—Young Law Firm, P.C.

(57) ABSTRACT

A needle is used to mark a tissue area of interest. The needle may have one or more indicators which indicate selected angular orientations relative to the needle. The indicators may also be coupled to anchors which are deployed in the tissue to anchor the needle in the tissue. The needle may be positioned to guide an excisional device to remove tissue.

58 Claims, 13 Drawing Sheets

U.S. PATENT DOCUMENTS

| | | | |
|---|---|---|---|
| 5,709,697 A | 1/1998 | Ratcliff | |
| 5,766,191 A | 6/1998 | Trerotola | |
| 5,794,626 A | 8/1998 | Kieturakis | |
| 5,895,399 A | 4/1999 | Barbut et al. | |
| 5,913,855 A | 6/1999 | Gough et al. | |
| 5,928,159 A | 7/1999 | Eggers et al. | |
| 5,928,164 A | 7/1999 | Burbank | |
| 5,947,964 A | 9/1999 | Eggers et al. | |
| 5,954,655 A | 9/1999 | Hussman | |
| 5,954,670 A | 9/1999 | Baker | |
| 6,015,390 A | 1/2000 | Krag | |
| 6,022,362 A | 2/2000 | Lee | |
| 6,036,708 A | 3/2000 | Sciver | |
| 6,063,082 A | 5/2000 | DeVore | |
| 6,080,149 A | 6/2000 | Huang | |
| 6,080,151 A | 6/2000 | Swartz et al. | |
| 6,096,053 A | 8/2000 | Bates | |
| 6,099,534 A | 8/2000 | Bates | |
| 6,106,524 A * | 8/2000 | Eggers et al. | 606/50 |
| 6,179,860 B1 | 1/2001 | Fulton, III et al. | |
| 6,221,006 B1 | 4/2001 | Dubrul et al. | |
| 6,238,389 B1 | 5/2001 | Paddock et al. | |
| 6,280,450 B1 * | 8/2001 | McGuckin, Jr. | 606/114 |
| 6,325,797 B1 | 12/2001 | Stewart et al. | |
| 6,331,166 B1 | 12/2001 | Burbank | |
| 6,383,145 B1 * | 5/2002 | Worm et al. | 600/564 |
| 6,387,056 B1 | 5/2002 | Kieturakis | |
| 6,405,733 B1 * | 6/2002 | Fogarty et al. | 128/899 |
| 6,514,248 B1 | 2/2003 | Eggers et al. | |
| 6,602,204 B2 | 8/2003 | Dubrul et al. | |
| 6,605,047 B2 | 8/2003 | Zarins et al. | |
| 2001/0047169 A1 | 11/2001 | McGuckin, Jr. | |
| 2002/0058885 A1 | 5/2002 | Burbank et al. | |

FOREIGN PATENT DOCUMENTS

| | | |
|---|---|---|
| EP | 0 829 232 A3 | 3/1998 |
| EP | 0 829 232 A2 | 3/1998 |
| EP | 0 908 156 B1 | 11/2003 |
| FR | 2 275 226 | 5/1975 |
| GB | 1 331 468 | 9/1973 |
| GB | 2 204 496 A | 11/1988 |
| GB | 2 311 468 A | 1/1997 |
| NL | 1.004723 | 9/1912 |
| SU | 1235497 A1 | 6/1986 |
| SU | 1355266 A1 | 11/1987 |
| WO | WO 92/20291 | 11/1992 |
| WO | WO 95/02370 | 1/1995 |
| WO | WO 95/02371 | 1/1995 |
| WO | WO 96/29946 | 10/1996 |
| WO | WO 98/08441 | 3/1998 |
| WO | WO 99/01074 | 1/1999 |
| WO | WO 99/04704 | 2/1999 |
| WO | WO 99/43262 | 9/1999 |
| WO | WO 99/44506 | 10/1999 |
| WO | WO 99/53851 | 10/1999 |
| WO | WO 00/10471 | 3/2000 |
| WO | WO 00/12009 | 3/2000 |
| WO | WO 00/16697 | 3/2000 |
| WO | WO 00/30531 | 6/2000 |
| WO | WO 00/33743 | 6/2000 |
| WO | WO 00/44295 | 8/2000 |
| WO | WO 00/45854 | 8/2000 |
| WO | WO 00/74561 A1 | 12/2000 |
| WO | WO 01/28445 A1 | 4/2001 |
| WO | WO 01/28446 A1 | 4/2001 |

* cited by examiner

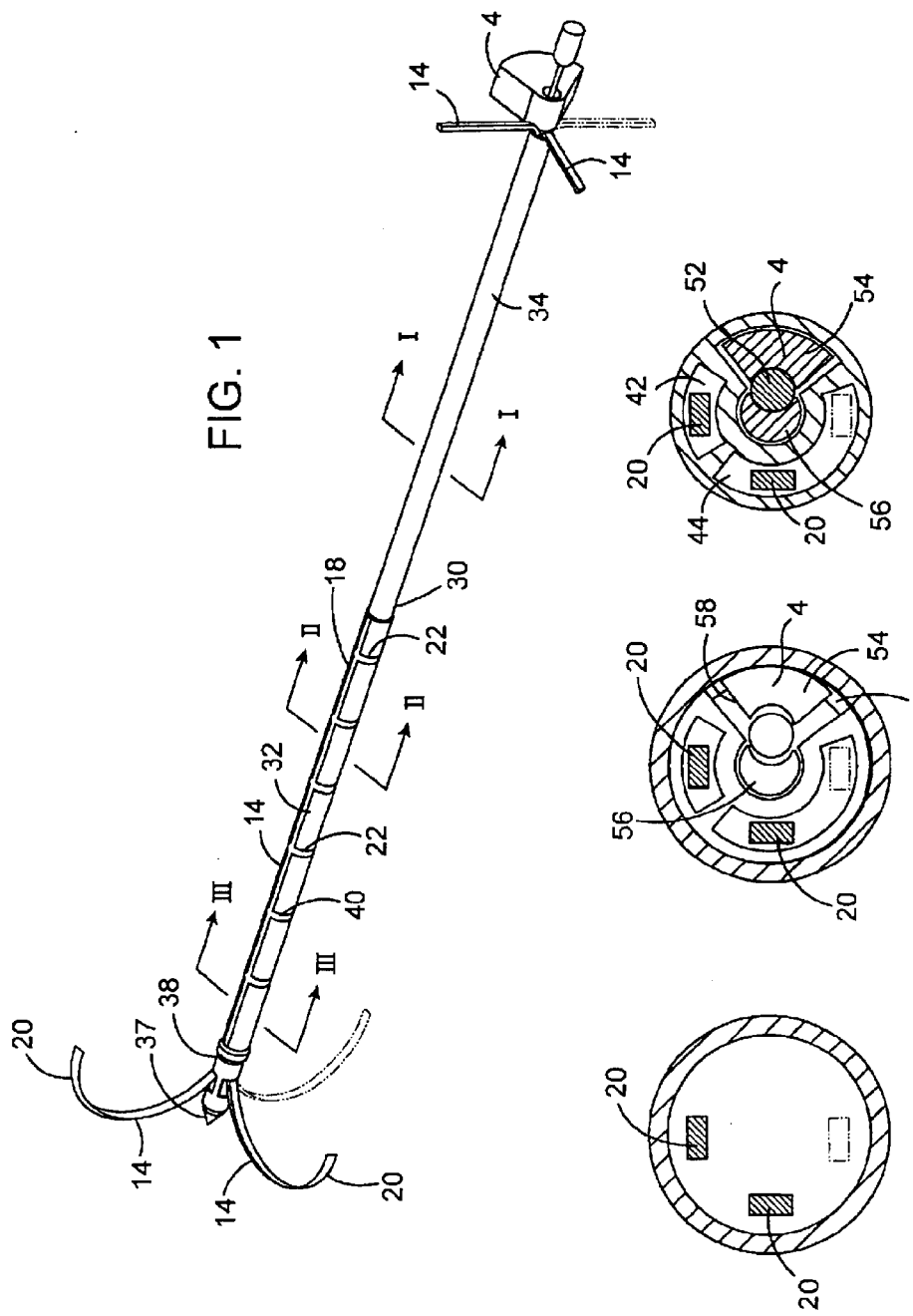

DEVICES AND METHODS FOR PERFORMING PROCEDURES ON A BREAST

BACKGROUND OF THE INVENTION

The present invention pertains to the field of marking tissue areas of interest. In a specific application, the present invention relates to the field of marking breast tissue for removal.

Breast cancer is a major threat and concern to women. Early detection and treatment of suspicious or cancerous lesions in the breast has been shown to improve long term survival of the patient. The trend is, therefore, to encourage women not only to perform monthly self-breast examination and obtain a yearly breast examination by a qualified physician, but also to undergo annual screening mammography commencing at age 40. Mammography is used to detect small, nonpalpable lesions which may appear opaque densities relative to normal breast parenchyma and fat or as clusters of microcalcifications.

The conventional method for diagnosing, localizing and excising nonpalpable lesions detected by mammography generally involves a time-consuming, multi-step process. First, the patient goes to the radiology department where the radiologist finds and localizes the lesion either using mammography or ultrasound guidance. Once localized, a radio-opaque wire is inserted into the breast. The distal end of the wire may include a small hook or loop. Ideally, this is placed adjacent to the suspicious area to be biopsied. The patient is then transported to the operating room.

Under general or local anesthesia, the surgeon may then perform a needle-localized breast biopsy. In this procedure, the surgeon, guided by the wire previously placed in the patient's breast, excises a mass of tissue around the distal end of the wire. The specimen is sent to the radiology department where a specimen radiograph is taken to confirm that the suspicious lesion is contained within the excised specimen. Meanwhile, the surgeon, patient, anesthesiologist and operating room staff, wait in the operating room for confirmation of that fact from the radiologist before the operation is completed.

The suspicious lesion should then be excised in toto with a small margin or rim of normal breast tissue on all sides. Obtaining good margins of normal tissue using conventional techniques is extremely dependent upon the skill and experience of the surgeon, and often an excessively large amount of normal breast tissue is removed to ensure that the lesion is located within the specimen. This increases the risk of post-operative complications, including bleeding and permanent breast deformity. As 80% of breast biopsies today are benign, many women unnecessarily suffer from permanent scarring and deformity from such benign breast biopsies.

More recently, less invasive techniques have been developed to sample or biopsy the suspicious lesions to obtain a histological diagnosis. The simplest of the newer techniques is to attempt visualization of the lesion by external ultrasound. If seen by external ultrasound, the lesion can be biopsied while being continuously visualized. This technique allows the physician to see the biopsy needle as it actually enters the lesion, thus ensuring that the correct area is sampled. Current sampling systems for use with external ultrasound guidance include a fine needle aspirate, core needle biopsy or vacuum-assisted biopsy devices.

Another conventional technique localizes the suspicious lesion using stereotactic digital mammography. The patient is placed prone on a special table that includes a hole to allow the breast to dangle therethrough. The breast is compressed between two mammography plates, which stabilizes the breast to be biopsied and allows the digital mammograms to be taken. At least two images are taken 30 degrees apart to obtain stereotactic views. The x, y and z coordinates targeting the lesion are calculated by a computer. The physician then aligns a special mechanical stage mounted under the table that places the biopsy device into the breast to obtain the sample or samples using fine needle aspiration, core needle biopsy, vacuum-assisted core needle biopsy or other suitable method. Fine needle aspiration uses a small gauge needle, usually 20 to 25 gauge, to aspirate a small sample of cells from the lesion or suspicious area. Core needle biopsy uses a larger size needle, usually 14 gauge to sample the lesion. Tissue architecture and histology are preserved with this method. Multiple penetrations of the core needle through the breast and into the lesion are required to obtain an adequate sampling of the lesion. Over 10 samples have been recommended by some. The vacuum-assisted breast biopsy system is a larger semi-automated side-cutting device. It is usually 11 gauge in diameter and is more sophisticated than the core needle biopsy device. Multiple large samples can be obtained from the lesion without having to reinsert the needle each time. A vacuum is added to suck the tissue into the trough. The rapid firing action of the spring-loaded core needle device is replaced with an oscillating outer cannula that cuts the breast tissue off in the trough. The physician controls the speed at which the outer cannula advances over the trough and can rotate the alignment of the trough in a clockwise fashion to obtain multiple samples.

If a fine needle aspirate, needle core biopsy or vacuum-assisted biopsy shows malignancy or a specific benign diagnosis of atypical hyperplasia, then the patient needs to undergo another procedure, the traditional needle-localized breast biopsy, to fully excise the area with an adequate margin of normal breast tissue. Sometimes the vacuum-assisted device removes the whole targeted lesion. If this occurs, a small titanium clip should be placed in the biopsy field. This clip marks the area if a needle-localized breast biopsy is subsequently required for the previously mentioned reasons.

Another method of biopsying the suspicious lesion utilizes a large end-cutting core device measuring 0.5 cm to 2.0 cm in diameter. This also uses the stereotactic table for stabilization and localization. After the lesion coordinates are calculated and local anesthesia instilled, an incision large enough is permit entry of the bore is made at the entry site with a scalpel. The breast tissue is cored down to and past the lesion. Once the specimen is retrieved, the patient is turned onto her back and the surgeon cauterizes bleeding vessels under direct vision. The incision, measuring 0.5 to larger than 2.0 cm is sutured closed.

The newer conventional minimally invasive breast biopsy devices have improved in some ways the ability to diagnose mammographically detected nonpalpable lesions. These devices give the patient a choice as to how she wants the diagnosis to be made.

SUMMARY OF THE INVENTION

In a first aspect of the present invention, a needle is provided for performing a procedure on a patient's breast. The needle has a proximal portion and a distal portion. The proximal portion is movable between a rigid condition and a flexible condition which may be selected by the user.

After introduction into the patient's breast, the proximal portion is made flexible. As mentioned above, needles are often introduced into the patient to mark an area of interest. The needle is introduced in one room of the hospital or clinic and the patient is then moved elsewhere, such as a surgical room, for a procedure. When moving the patient between these locations, a rigid needle protruding from the breast can cause obvious problems from inadvertent contact. The present invention provides the ability to provide a flexible proximal portion which is less susceptible to inadvertent bumping and is less obtrusive to the patient and medical personnel. The needle may penetrate some of the tissue being removed or may penetrate only tissue which is not being removed. The needle may also be made rigid again before performing the medical procedure or the medical procedure may be carried out with the proximal portion flexible.

In another aspect of the present invention, the needle may also have one or more indicators for indicating angular orientations relative to a longitudinal axis of the needle. The angular information may be used for any suitable procedure including removal of breast tissue. The indicator may be coupled to an anchoring element which may be deployed at the same angular position. The anchor may be any suitable element such as a wire.

In still another aspect of the present invention, a guide element, such as the needle, guides a tissue removing device. The guide element may provide indications as to the area of the breast tissue to be removed. For example, the guide element may have depth markers or may have the indicators described above which mark angular positions. The guide element may also constrain the cutting device with a longitudinal stop and one or more angular stops which prevent rotation beyond one or more angular positions. When removing tissue, the cutting device may also have a collection element, such as a bag, which collects the severed tissue for removal.

These and other aspects of the present invention will become apparent from the following drawings and description.

BRIEF DESCRIPTION OF THE DRAWINGS

FIG. 1 shows a needle made in accordance with the present invention.

FIG. 2 is a cross-sectional view of the device along line I—I of FIG. 1.

FIG. 3 is a cross-sectional view of the device along line II—II of FIG. 1.

FIG. 4 is a cross-sectional view of the device along line III—III of FIG. 1.

DESCRIPTION OF THE PREFERRED EMBODIMENT

Figure 12:
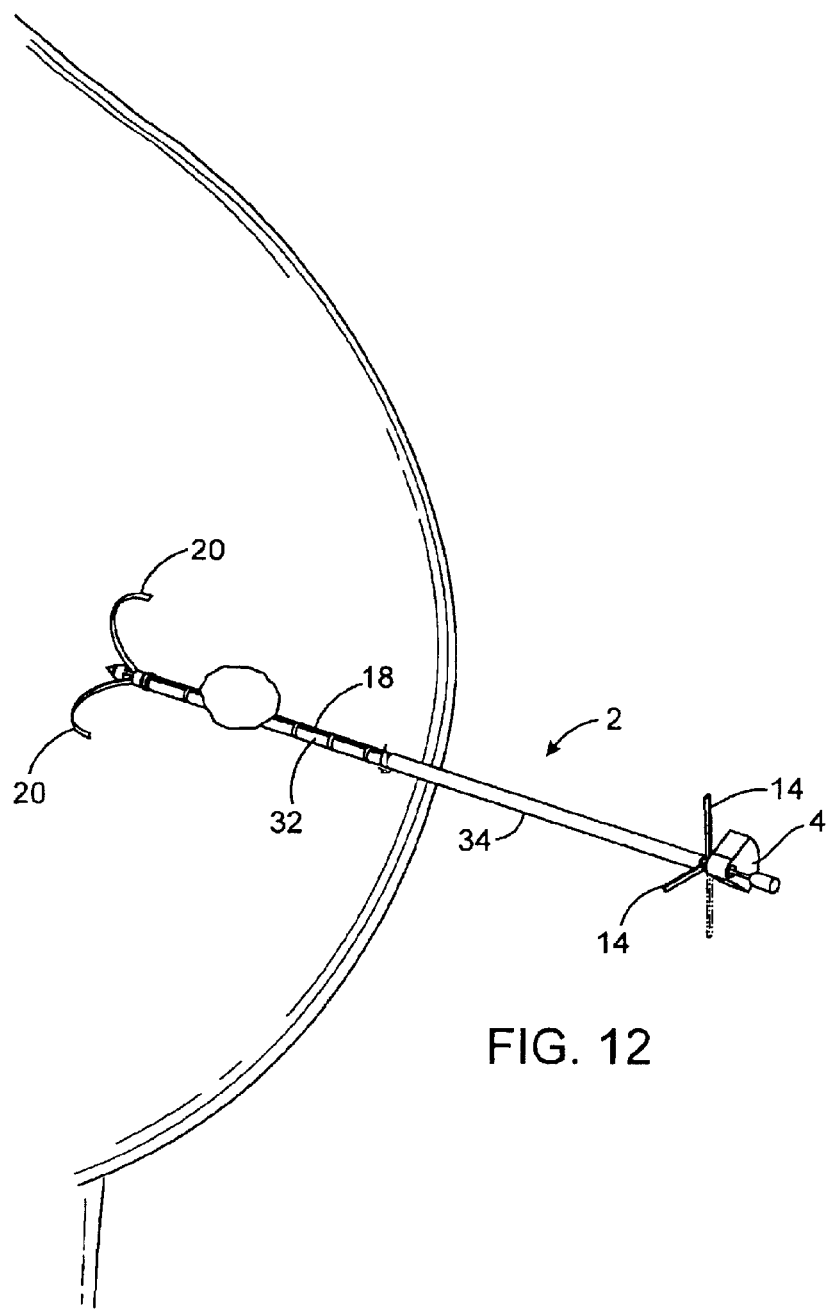
FIG. 12 shows a second anchor deployed within the breast.

Referring to FIGS. 1 and 10–14, a needle 2 made in accordance with the present invention is shown. The needle 2 may be used to perform or help perform any procedure anywhere in the body. As an example of one such procedure, the needle 2 may be used to mark the location of a tissue area of interest such as a tissue area to be removed. In a specific example, the needle 2 is used to mark breast tissue which is to be removed (FIG. 12). The term "needle" as used herein shall mean any device having an elongate shaft. Of course, as with the exemplary embodiment, the device 2 may have actuators, manipulators, ablation elements, RF, ultrasound, or other functionality without departing from the scope of the invention.

Figure 13:
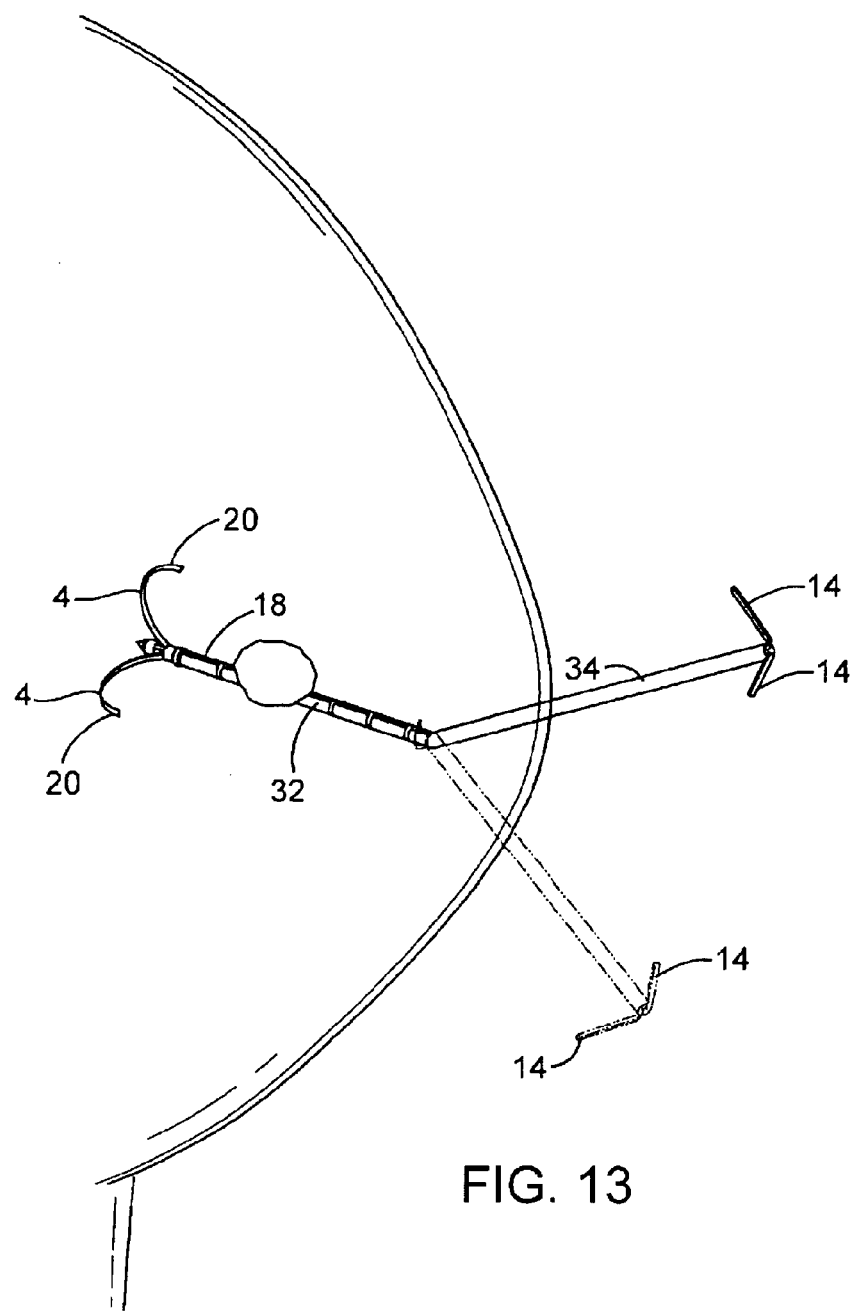
FIG. 13 shows a stiffener removed to provide a flexible proximal end.
Figure 14:
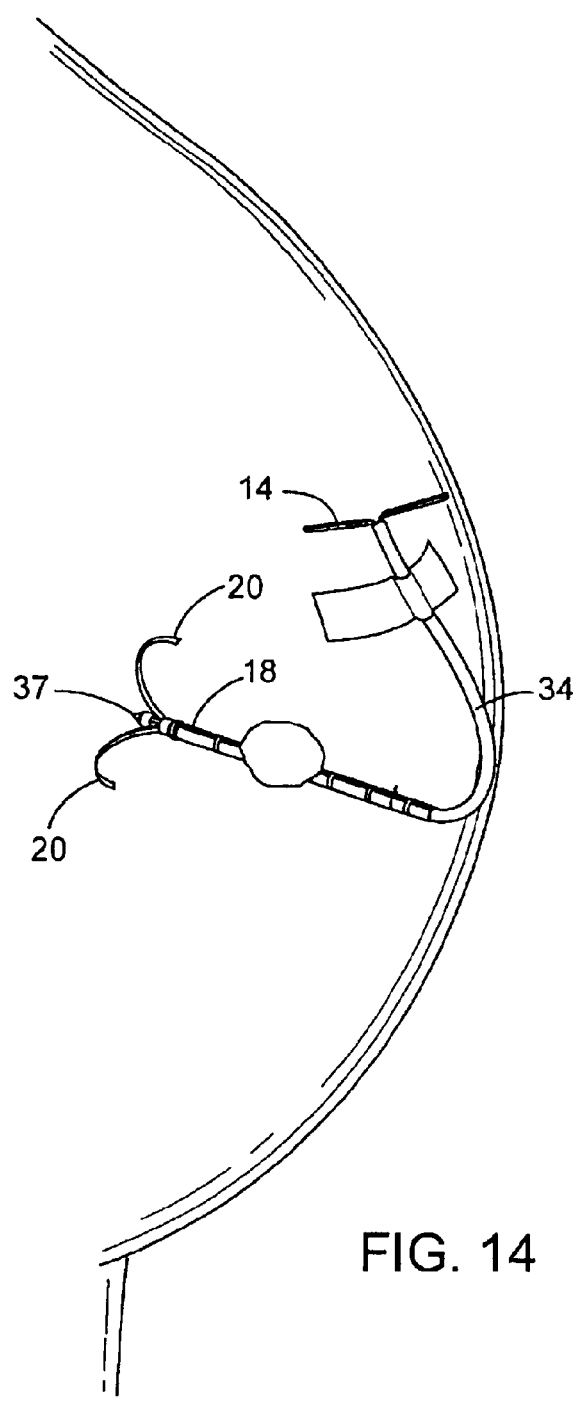
FIG. 14 shows the flexible, proximal portion taped to the breast.

The needle 2 may be introduced in the breast in a rigid condition to facilitate introduction and then changed to a more flexible condition. As mentioned above, conventional needles are often introduced into the patient to mark a tissue area of interest such as a tissue area to be removed. The needle is often introduced in one room of the hospital or clinic where the area of interest can be visualized during introduction. After the needle has been introduced, the procedure takes place elsewhere such as in a surgical room. When moving the patient between these locations, a rigid needle protruding from the breast can present obvious problems with respect to inadvertent contact. The present invention provides the ability to make part of the needle 2 flexible so that the flexible part of the needle 2 can be moved out of the way or even taped to the patient (FIGS. 13 and 14). The needle 2 may or may not penetrate the tissue being removed depending upon the particular procedure performed. The flexible part of the needle 2 may provide other advantages as described below.

The needle 2 may be changed between the rigid and flexible conditions using any suitable structure such as a removable stiffener 4. After removal of the stiffener 4, the rigid condition may be restored at a later time by simply replacing the stiffener 4. When using the needle 2 to manipulate tissue being cut, it may be advantageous to maintain the flexible condition to apply tension at varying angles depending upon the area being cut. This provides obvious advantages over conventional rigid needles (see dotted-line position of FIG. 13). One such system permanently anchors the needle to the tissue with wires fused to the tissue using RF energy. The rigid needle is then manipulated while cutting and removing tissue around the needle and wires.

Figure 5:
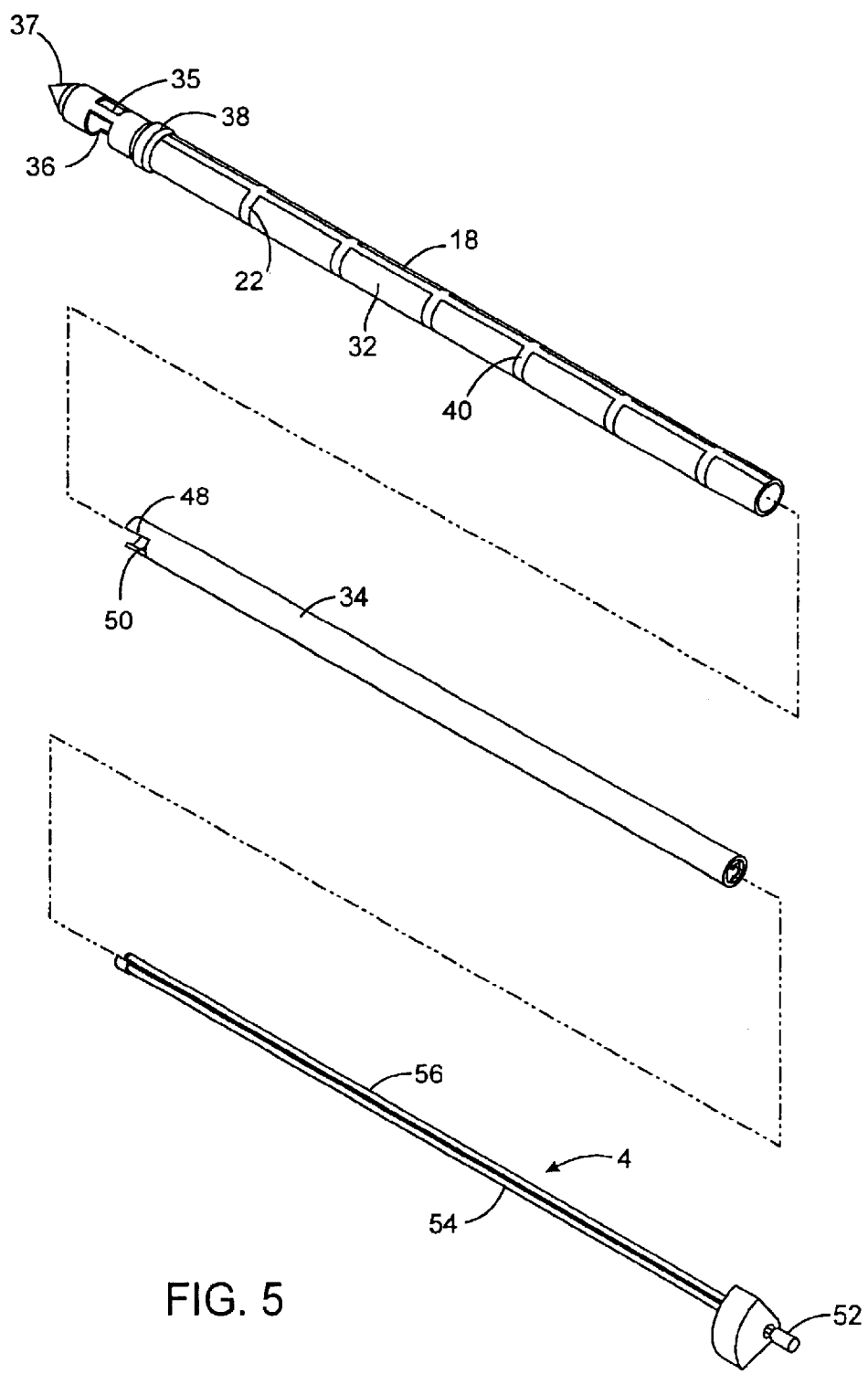
FIG. 5 is an exploded view of the shaft and locking mechanism.
Figure 6:
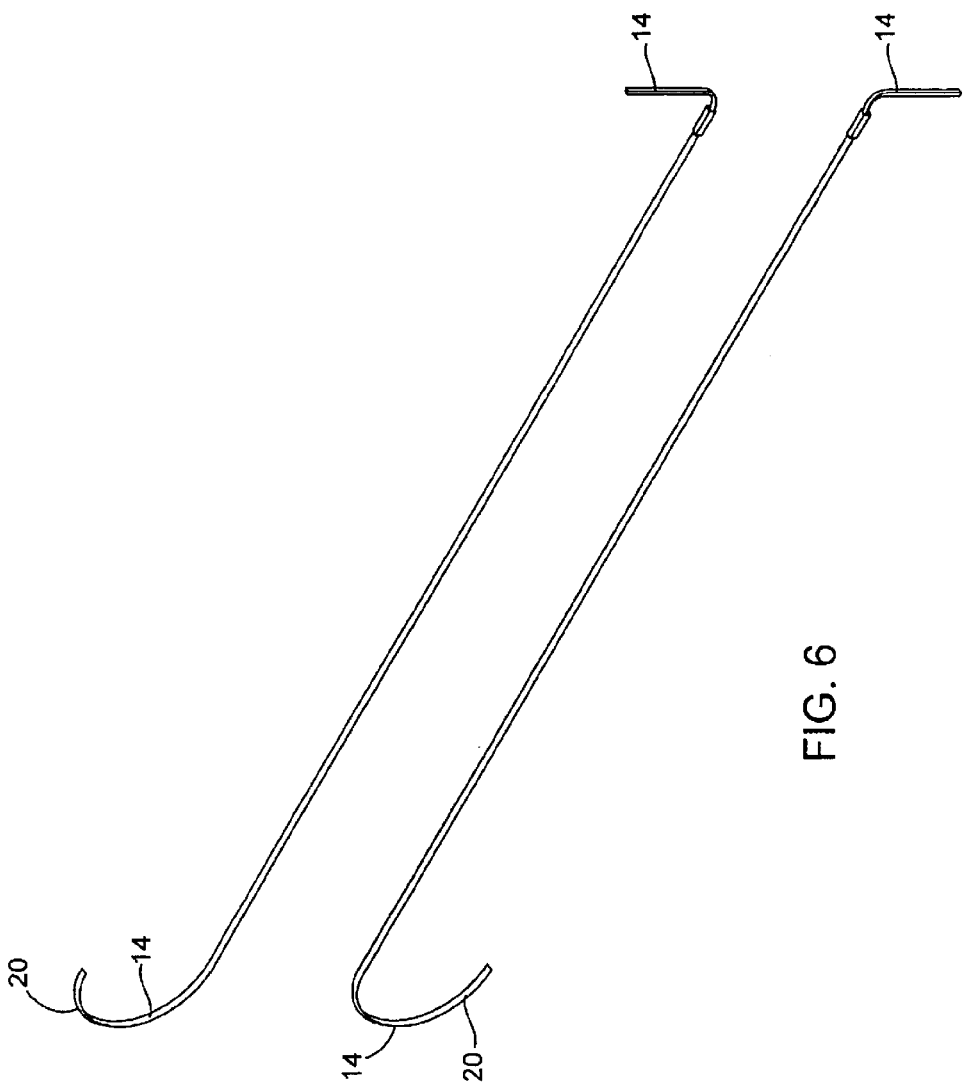
FIG. 6 shows the anchors.
Figure 7:
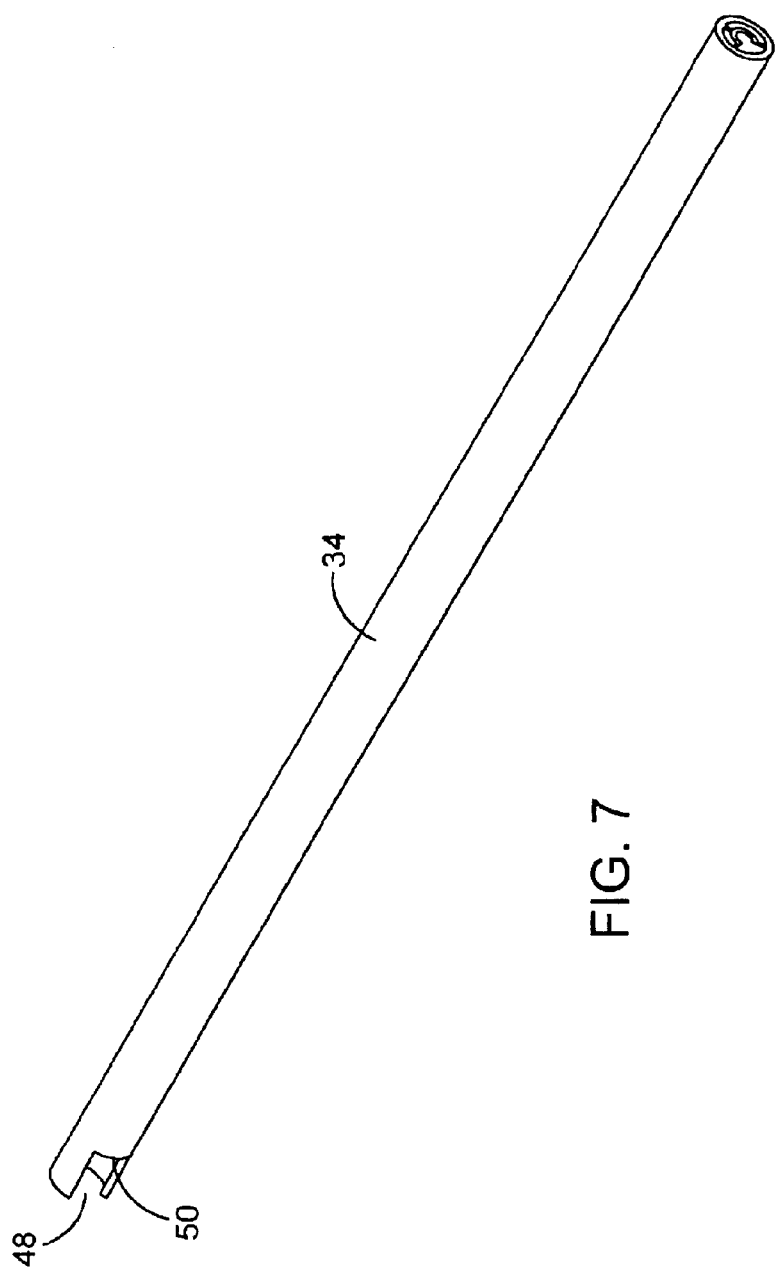
FIG. 7 shows the flexible portion of the shaft.
Figure 8:
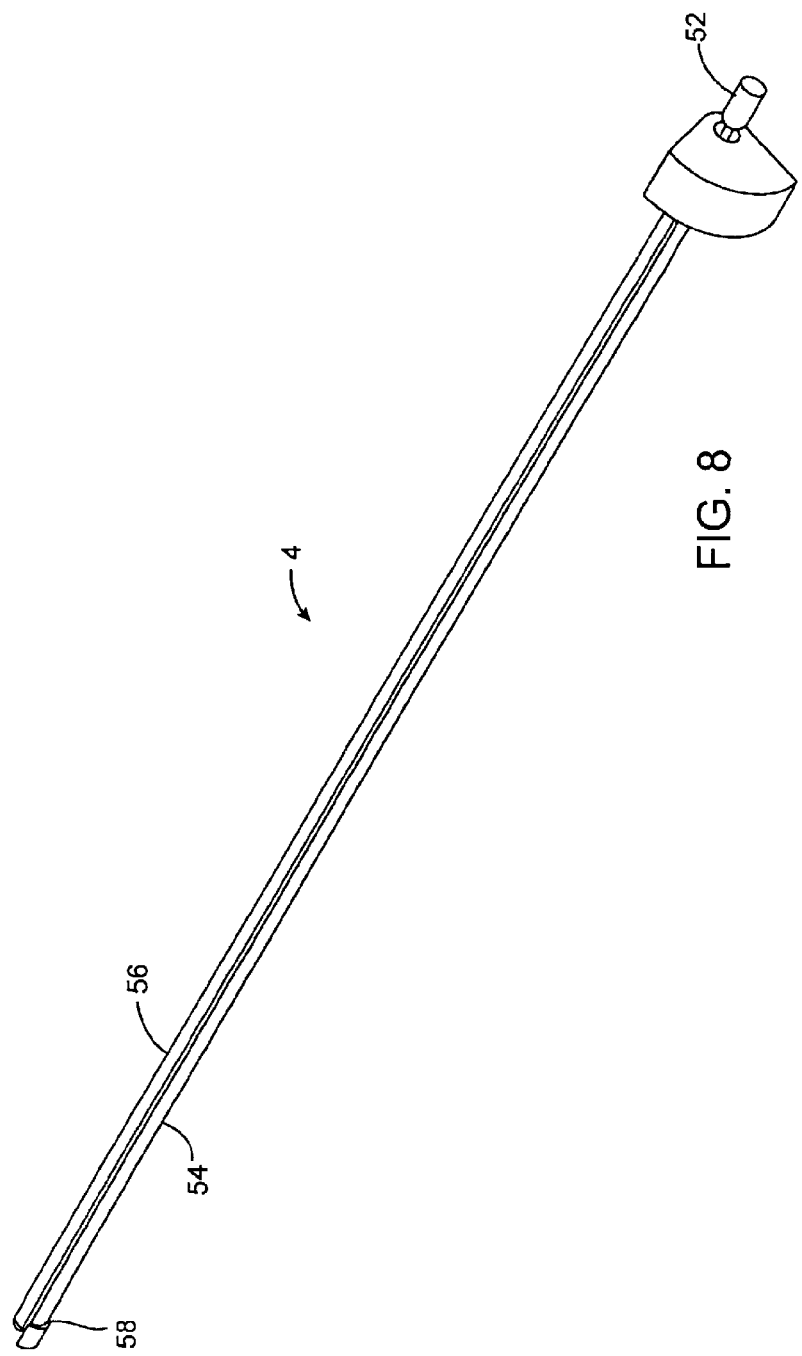
FIG. 8 shows the locking mechanism.
Figure 9:
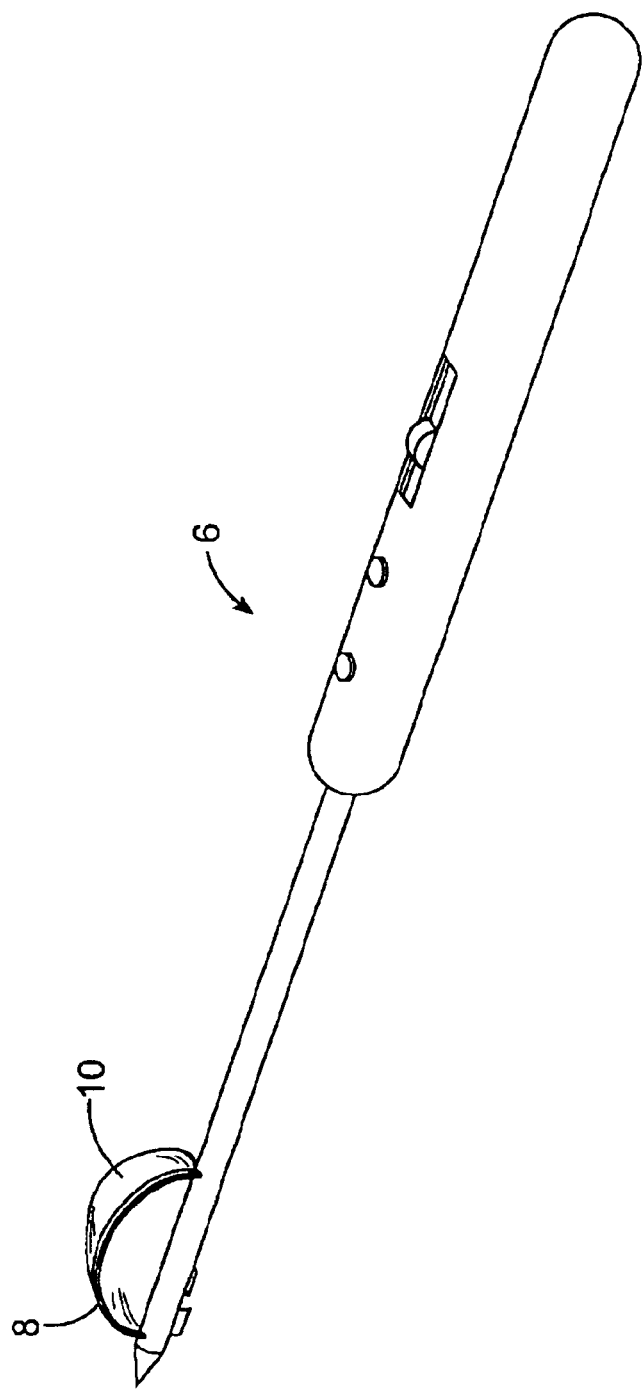
FIG. 9 shows a tissue removing device.
Figure 10:
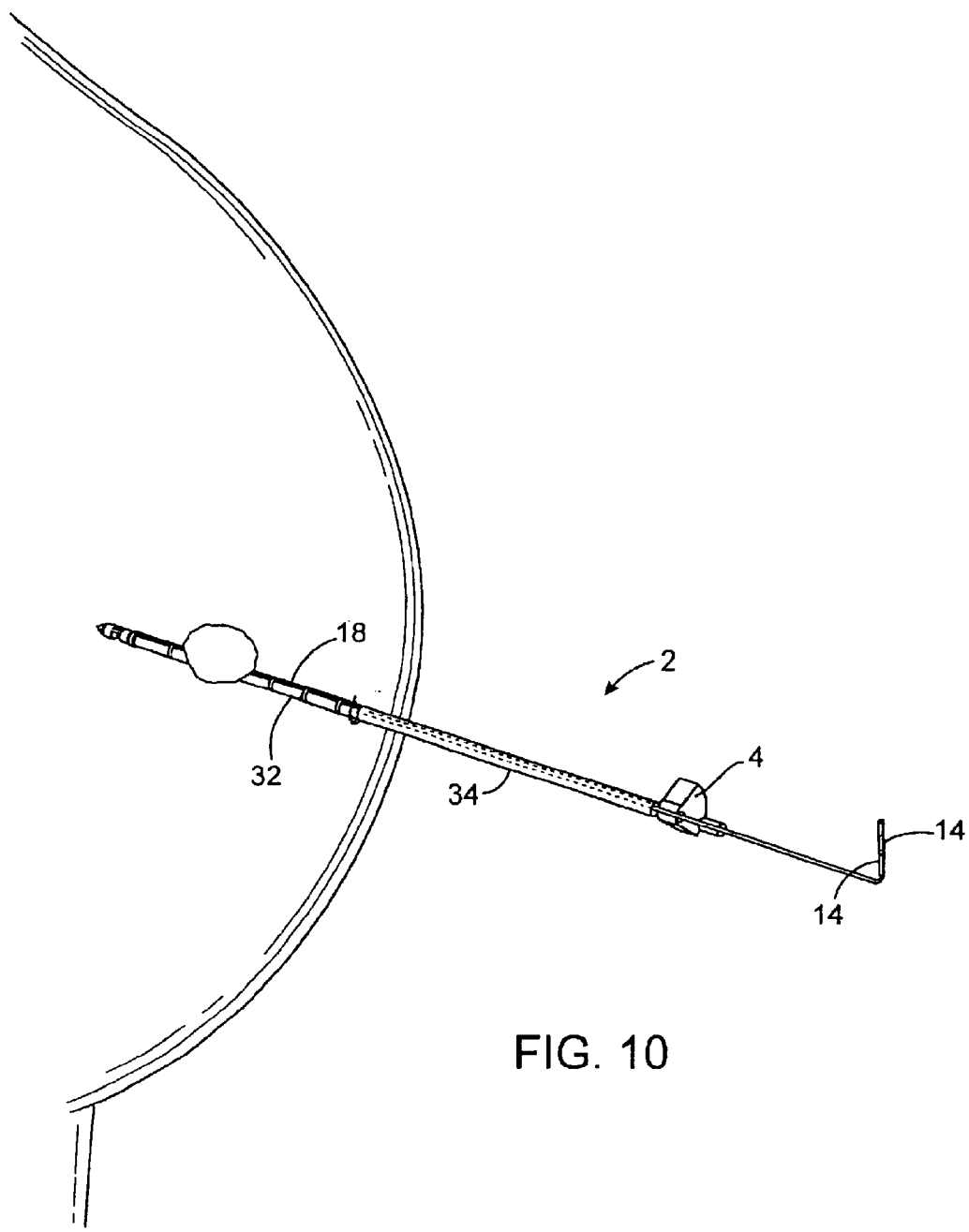
FIG. 10 shows the needle introduced into a breast.
Figure 11:
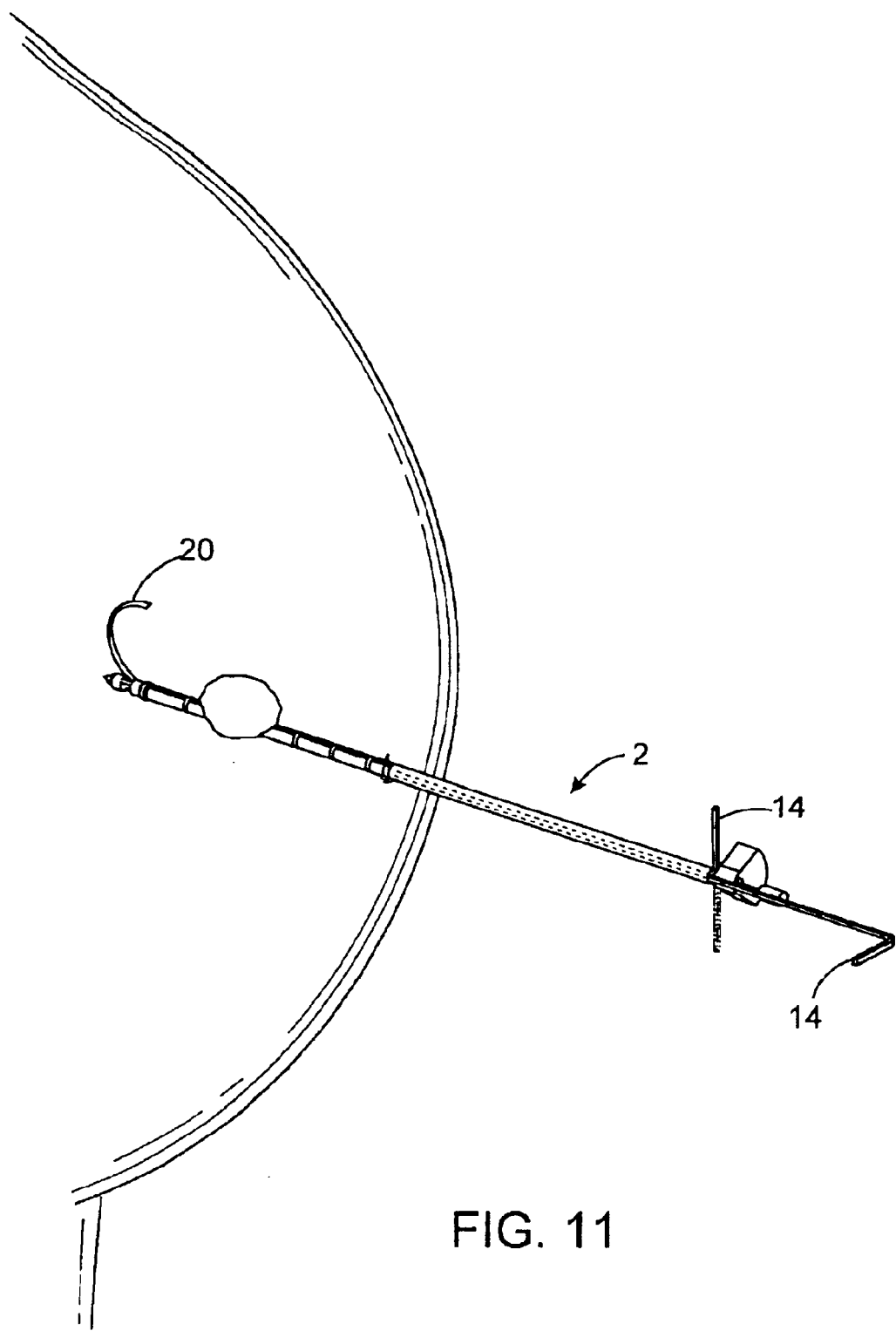
FIG. 11 shows a first anchor deployed within the breast.
Figure 15:
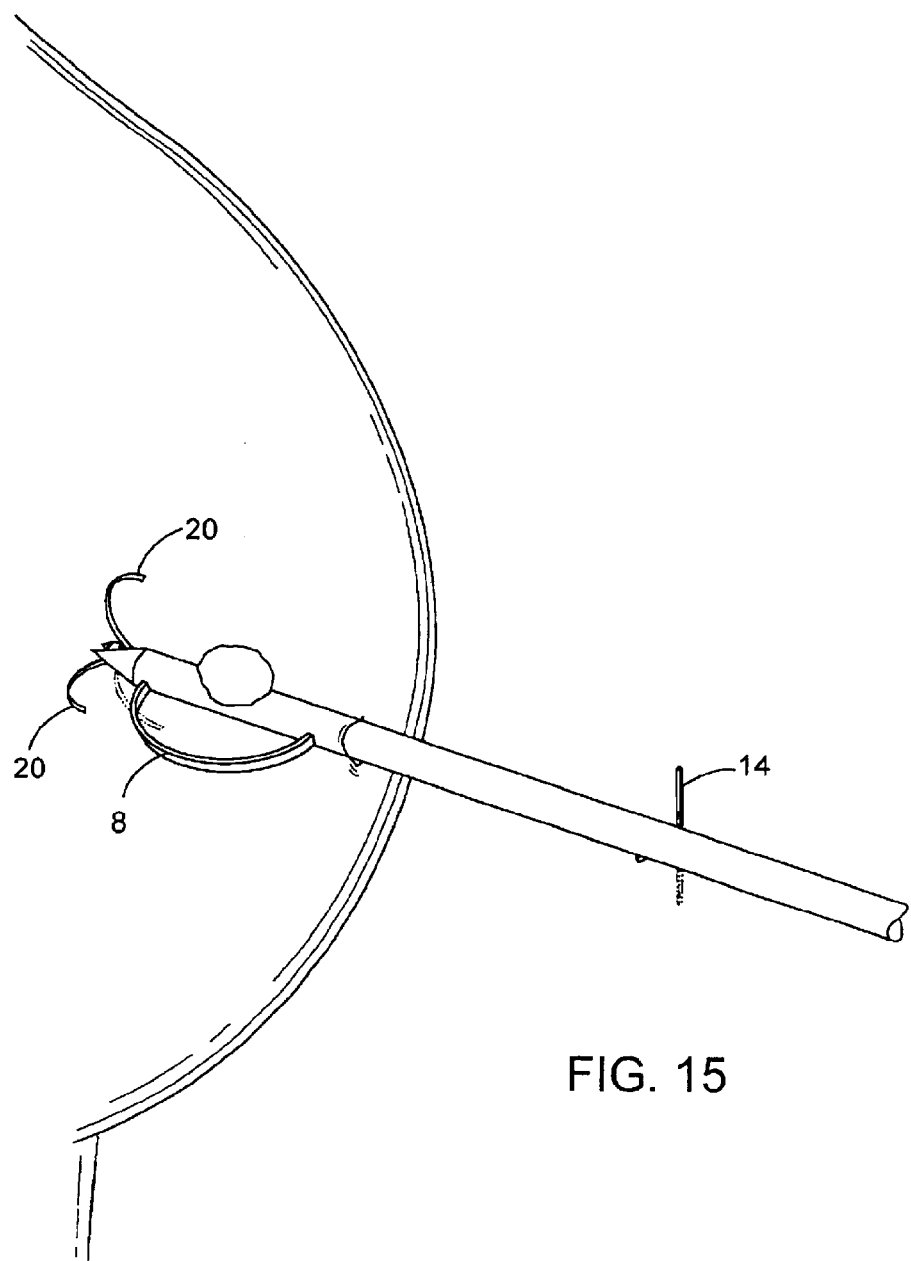
FIG. 15 shows a tissue removing device advanced over the needle and a cutting element deployed.
Figure 16:
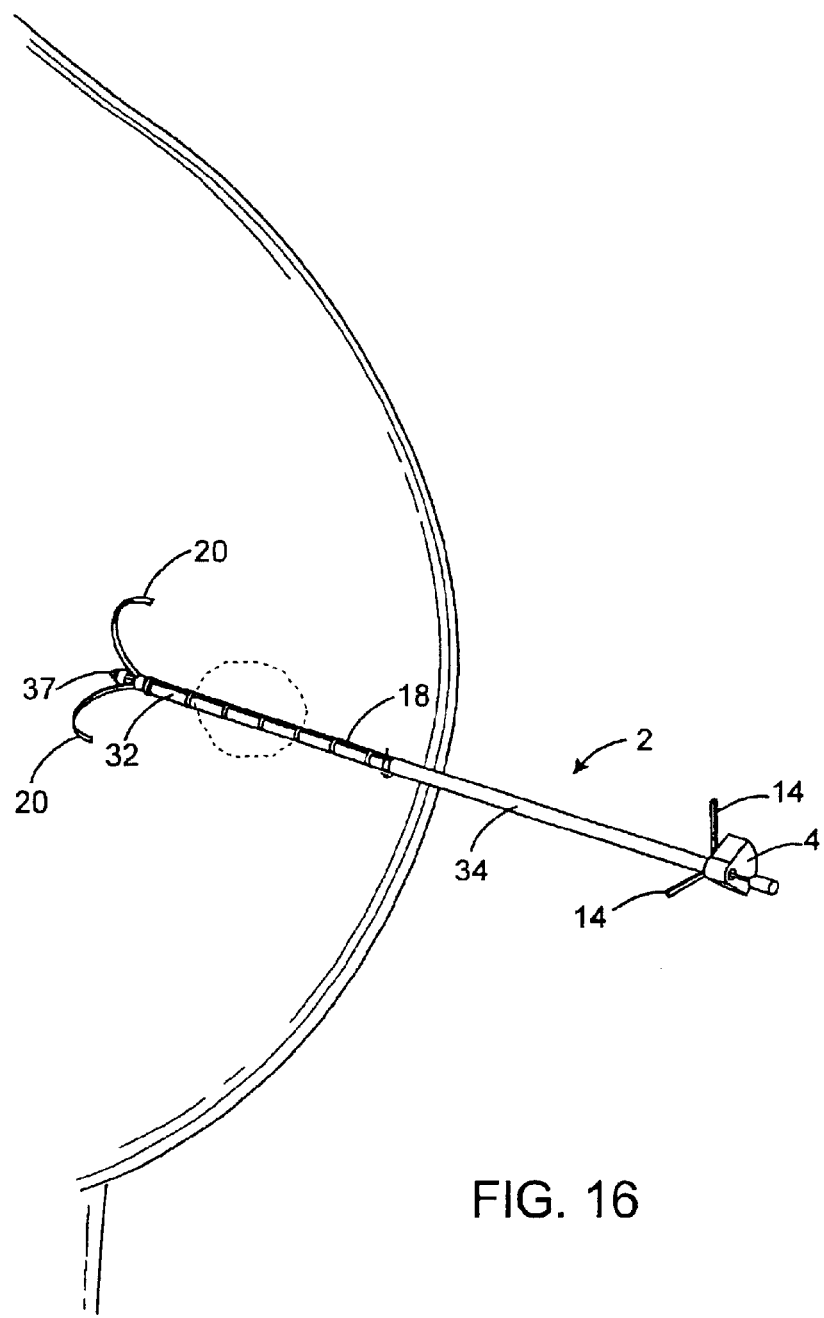
FIG. 16 shows a void where the tissue removing device has removed the tissue area of interest.

Referring to FIGS. 9 and 15, the needle 2 may also be used to guide another medical device such as a tissue cutting device 6. Any suitable tissue cutting device may be used and one of particular device interest is disclosed in U.S. Pat. Nos. 6,440,147 and 6,022,362 which are hereby incorporated by reference. The tissue cutting device 6 has a cutting element 8 movable between collapsed and bowed positions. The tissue cutting device 6 is pivoted or rotated so that the cutting element 8 sweeps through and cuts the tissue along an arc. A tissue collection element 10 may also be provided which collects the tissue being cut.

Referring now to FIGS. 1, 5, 6 and 10, the needle 2 may have an indicator 14 to mark an angular position relative to the longitudinal axis 16 of the needle 2. The indicator 14 extends radially outward from the needle at a angle selected by the user. The indicator 14 may also simply be a longitudinal stripe 18 or other marking on the shaft which indicates a particular angular orientation on the needle 2. The indicator 14 may provide information to the user regarding various parameters depending upon the procedure being performed. For example, when using the device 6 described above, the angular position, or positions, provide the user with the angular extent of the tissue to be removed.

The indicators 14 may be coupled to one more anchors 20 which are deployed to anchor the needle 2. The anchor 20 is preferably curved, such as J- or C-shaped, and extends radially to lie within the same angular orientation as the indicator 14. An advantage of coupling the indicator 14 to the anchor 20 is that anchor 20 itself provides information regarding the relative orientation or the needle 2, anchor 20 and tissue area of interest Thus, the anchor 20 itself may be one of the indicators 14. Although the anchor 20 and indicator 14 are preferably aligned at the same angular orientation, they may also be offset to account for the geometry of other devices used with the needle 2. As can be appreciated, of course, the indicators 14 may also be independent of any anchoring elements. For example, the needle 2 may be placed in the breast and the indicators 14 could then be moved to selected angular position(s). The needle 2 may also have depth markers 22 along the body. The anchor 20 is preferably a stainless steel wire having a sharpened tip to pierce through the tissue. The orientation of the anchor 20 is partially guided by the geometry of the arc-shaped lumens receiving the anchors 20 (FIGS. 2 and 3).

As can be appreciated, the various aspects of the present invention may be practiced using many different physical configurations without departing from the scope of the invention. Thus, the following preferred embodiment is not intended to limit the scope of the invention. Referring to FIGS. 1–8, the needle 2 has a shaft 30 having a rigid tube 32 coupled to a flexible tube 34. The rigid tube 32 has a sharp tip 37 to pierce tissue. The rigid tube 32 is preferably a hypotube of stainless steel having a size of 18 GA to 12 GA such as 16 GA. The rigid tube 32 has two openings 35, 36 or slots at or near the distal end through which the anchors 20 extend. The first opening 35 is radially smaller than the second 36 since the anchor 20 is deployed at a predetermined angular orientation aligned with the longitudinal marker or stripe 18. Of course, the needle 2 may be configured with both anchors 20 rotatable or pivotable within the openings 35, 36. The tube 32 also has a stop 38 which prevents further longitudinal movement of the tissue cutting device 6 and markers 40 for providing depth information.

Referring to FIGS. 1–8, the flexible tube 34 may be a three-lumen extrusion. The first and second lumens 42, 44 each receive one of the anchors 20 and the third lumen 46 receives the stiffener 4. The flexible tube 34 is bonded to the rigid tube 32 in any suitable manner such as with an adhesive. The flexible tube 34 is sized to fit within the rigid tube 32. A portion of the side wall around the stiffener 4 is removed to form a cut-out 48 having a shoulder 50 to lock the stiffener 4 as now described Referring to FIGS. 1, 5, 7 and 8, the stiffener 4 is shown. Of course, any type of stiffening device may be used. An actuator 52, which may simply be an elongate rod, is advanced to expand and open first and second prongs 54, 56 at the distal end of the stiffener 4. The first prong 54 has a shoulder 58 which engages the shoulder 50 formed by the cut-out 48 portion of the tube 34. Alternatively, the shoulder 50 may, of course, also be formed by the rigid tube 32 or a piece of material attached to inner surface of the rigid tube 32. When the actuator 52 is withdrawn, the prongs 54, 56 naturally collapses so that the shoulders 50, 58 do not engage and the stiffener may be removed. FIG. 14 shows the proximal portion taped to the patient after removing the stiffener 4. FIG. 13 also shows the flexible portion being tensioned in different directions.

Use of the device is now described in connection with a tissue removal procedure with reference to FIGS. 1 and 9–16. Of course, other procedures may be performed without departing from the scope of the invention. The needle 2 is introduced into the area of interest under suitable visualization such as ultrasound. Once the needle 2 has been introduced in a desired or known orientation relative to the tissue area of interest, the entire needle 2 is rotated so that the first indicator 14 and marker 18 are aligned with a first angular position relative to the tissue area of interest. The first anchor 20 is then deployed into the tissue with the anchor 20 deployed at the selected angular orientation. The second indicator 14 is then rotated to a second selected angular orientation with respect to the area of interest. The second orientation is determined by visualizing the area of interest relative to the needle 2 and/or first anchor 20 to determine the appropriate location for the second anchor 20. The second anchor 20 is then deployed by advancing the anchor into the tissue. As can be appreciated, the needle 2 and anchors 20 themselves provide visual landmarks for locating the area of interest. The markings on the needle 2 and the indicators 14 also help to guide use of the tissue cutting device 6 as described herein.

The stiffener 4 is then removed to provide the flexible proximal portion. The flexible proximal portion may be taped to the patient to prevent inadvertent contact as shown in FIG. 14. When performing the procedure, the flexible condition may be maintained to provide the benefit described above such as the ability to pull from varying angles as compared to a conventional rigid needle. The tissue removal device 6 may then be coupled to the needle 2 as shown in FIG. 15 and then advanced while being guided by the needle 2. The needle 2 may be introduced to a predetermined depth where the longitudinal stop 38 guides the depth of introduction of the tissue removal device. Of course, the needle 2 may be introduced deeper into the tissue with the user using the depth markings 40 on the needle 2 and/or tissue removal device 6 to determine the appropriate introduction depth for the tissue removal device 6. The cutting element 8 is then deployed to the bowed position and the cutting element 8 is swept through tissue to cut around the tissue area of interest. The tissue is then collected by the collection element 10 for removal. The device 6 is then withdrawn and the anchors 30 are retracted to permit withdrawal of the needle 2 as well.

As can be appreciated, the present invention can be practiced in many different forms and for many different procedures. Furthermore, the aspects of the invention are distinct. For example, the present invention provides a flexible proximal portion which is distinct from the ability to mark angular orientations. Thus, each feature of the present invention are independent of one another. Finally, numerous physical modifications may be made without departing from the scope of the invention. For example, the anchors may be spikes, an expandable mesh, prongs, or a helical screw and the cutting device may be a wire cage, a multiple-bladed cutter, or simply a scalpel without departing from numerous aspects of the invention.

What is claimed is:

1. A method of positioning a needle in a patient's breast for a medical procedure, comprising the steps of:

providing a needle having a proximal portion and a distal portion, the proximal portion being movable between a rigid condition and a flexible condition which may be selected by a user;

positioning the distal portion in a patient's breast with the proximal portion remaining outside the breast, the distal portion being in the rigid condition for facilitating introduction into the patient's breast;

changing the proximal portion from the rigid condition to the flexible condition after the positioning step; and performing a medical procedure on the patient's breast.

2. The method of claim 1, wherein:

the performing step includes the step of removing breast tissue.

3. The method of claim 2, wherein:

the performing step is carried out by removing tissue not penetrated by the needle.

4. The method of claim 1, further comprising the step of:

creating another rigid condition at the proximal portion after the changing step and before the performing step.

5. The method of claim 1, wherein:

the changing step is carried out by removing a stiffener from the proximal portion of the needle.

6. The method of claim 1, wherein:

the performing step is carried out by guiding a cutting device into the patient using the needle to guide the cutting device.

7. The method of claim 1, wherein:

the performing step is carried out with a tissue removal device being guided by the needle and the medical procedure being a tissue removal procedure.

8. The method of claim 7, wherein:

the performing step is carried ant with the tissue removal device rotating to move a cutting element along an arc within the tissue.

9. The method of claim 7, wherein:

the performing step is carried out with the tissue removal device being rotationally constrained by the needle at a first location.

10. The method of claim 9, wherein:

the performing step is carried out with the first location coinciding with a first angular indicator which indicates an angular position with respect to a longitudinal axis of the needle to the user.

11. The method of claim 7, wherein:

the performing step is carried out with the tissue removal device having a cutting element which moves between bowed and retracted positions, the cutting element being in a bowed position while cutting tissue.

12. The method of claim 7, wherein:

the performing step is carried out with the tissue removal device engaging a stop on the needle which prevents farther longitudinal movement of the tissue removal device.

13. The method of claim 12, wherein:

the performing step is carried out with the stop positioning the tissue removal device in a predetermined longitudinal position.

14. The method of claim 1, further comprising the step of:

moving an indicator on the needle, the indicator being moved to a position which indicates an angular position with respect to a longitudinal axis of the needle.

15. The method of claim 14, wherein:

the moving step is carried out with the position of the indicator providing an angular bound of tissue to be removed from the breast.

16. A needle for marking a patient's breast when performing a medical procedure on the patient, comprising:

a distal portion having an elongate, rigid shaft; and a proximal portion coupled to the distal portion, the proximal portion being selectively movable between a rigid condition and a flexible condition, wherein the proximal portion is in the rigid condition during introduction into a patient's breast and is movable to the flexible condition after introduction into the breast.

17. The needle of claim 16, wherein:

the proximal portion has a removable stiffener.

18. The needle of claim 16, further comprising:

an indicator which is movable to a selected angular orientation relative to a longitudinal axis.

19. The needle of claim 16, wherein:

the needle has a longitudinal stop which prevents further longitudinal movement of a tissue removal device, the stop being oriented to position the tissue removal device in a predetermined longitudinal position relative to the tissue be removed after positioning the needle in the breast.

20. The needle of claim 16, further comprising:

an anchoring element which is movable together with the indicator to a selected orientation relative to the longitudinal axis.

21. The needle of claim 20, wherein:

the anchoring element is a thin, elongate element which pierces the breast tissue.

22. The needle of claim 21, further comprising:

a shaft having an opening;

the element extends through the opening in the shaft.

23. The needle of claim 20, wherein:

the anchoring element is a J-shaped wire.

24. A method of positioning a needle in a patient's breast for a medical procedure, comprising the steps of:

providing a needle having at least one movable indicator for indicating an angular orientation when viewed along a longitudinal axis of the needle, the needle having a distal portion and a proximal portion;

positioning the distal portion in a patient's breast with the proximal portion remaining outside the breast, moving the indicator to a position which provides an indication of a selected angular orientation relative to the longitudinal axis to move the indicator to a position which angularly bounds a tissue area to be removed from the breast, and performing a medical procedure using information from the selected angular orientation.

25. The method of claim 24, wherein:

the performing step includes the step of removing breast tissue.

26. A method of positioning a needle in a patient's breast for a medical procedure, comprising the steps of:

providing a needle at least one movable indicator for indicating an angular orientation when viewed along a longitudinal axis of the needle, the needle having a distal portion that includes at least one anchoring element and a proximal portion;

positioning the distal portion in a patient's breast with the proximal portion remaining outside the breast, moving the indicator to a position which provides an indication of a selected angular orientation relative to the longitudinal axis, the moving step being carried out by moving the at least one anchoring element, the at least one anchoring element being displaced angularly with respect to the longitudinal axis, and performing a medical procedure using information from the selected angular orientation.

27. The method of claim 26, wherein:
the performing step includes the step of removing breast tissue.

28. The method of claim 26, wherein:
the moving step is carried out with the at least one anchoring element being a thin, elongate element which pierces the breast tissue.

29. The method of claim 26, wherein:
the moving step is carried out with the at least one anchoring element being a wire.

30. The method of claim 28, wherein:
the providing step is carried out with the needle having a shaft; and
the moving step is carried out with the anchoring element extending through a slot in the shaft.

31. The method of claim 28, wherein:
the performing step includes the step of removing breast tissue.

32. A method of positioning a needle in a patient's breast for a medical procedure, comprising the steps of:
providing a needle having at least one movable indicator for indicating an angular orientation when viewed along a longitudinal axis of the needle, the needle having a distal portion and a proximal portion;
positioning the distal portion in a patient's breast with the proximal portion remaining outside the breast,
moving the indicator to a position which provides an indication of a selected angular orientation relative to the longitudinal axis by selecting at least two different angular positions when viewed along the longitudinal axis of the needle, and
performing a medical procedure using information from the selected angular orientation.

33. The method of claim 32, wherein:
the performing step includes the step of removing breast tissue.

34. The method of claim 32, wherein:
the providing is carried out with the needle including at least one anchoring element, and
the moving step is carried out by moving the at least one anchoring element, the anchoring element being displaced angularly with respect to the longitudinal axis during the moving step.

35. The method of claim 34, wherein:
the moving step is carried out with the at least one anchoring element being a thin, elongate element which pierces the breast tissue.

36. The method of claim 34, wherein:
the moving step is carried out with the at least on anchoring element being a wire.

37. The method of claim 35, wherein:
the providing step is carried out with the needle having a shaft; and
the moving step is carried out with the element extending through a slot in the shaft.

38. A method of positioning a needle in a patient's breast for a medical procedure, comprising the stops of:
providing a needle having at least one movable indicator for indicating an angular orientation when viewed along a longitudinal axis of the needle, the needle having a distal portion and a proximal portion;
positioning the distal portion in a patient's breast with the proximal portion remaining outside the breast,
moving the indicator to a position which provides an indication of a selected angular orientation relative to the longitudinal axis and repeating the moving step at least once to indicate two different angular orientations relative to the longitudinal axis, and
performing a medical procedure using information from the selected angular orientation.

39. The method of claim 38, wherein:
the providing is carried out with the needle including at least one anchoring element, and
the moving step is carried out by moving the at least one anchoring element, the anchoring element being displaced angularly with respect to the longitudinal axis during the moving step.

40. The method of claim 39, wherein:
the moving step is carried out with the at least one anchoring element being a thin, elongate element which pierces the breast tissue.

41. The method of claim 39, wherein:
the moving step is carried out with the at least on anchoring element being a wire.

42. The method of claim 40, wherein:
the providing step is carried out with the needle having a shaft; and
the moving step is carried out with the element extending through a slot in the shaft.

43. A needle for introduction into a patient's breast, comprising:
an elongate shaft having a longitudinal axis; and
a first indicator for indicating an angular orientation when viewed along the longitudinal axis of the shaft, the first indicator being movable by the user to a selected angular orientation and being coupled to an anchoring element, the anchoring element being displaced angularly with respect to the longitudinal axis when the first indicator is moved by the user.

44. The needle of claim 43, wherein:
the first indicator is moved to a position to provide angular information regarding a tissue area to be removed from the breast.

45. The needle of claim 43, wherein:
the anchoring element is a thin, elongate element which pierces the breast tissue.

46. The needle of claim 43, wherein:
the anchoring element is a wire.

47. The needle of claim 46, wherein:
the wire extending through a slot in the shaft.

48. A needle for introduction into a patient's breast, comprising:
an elongate shaft having a longitudinal axis;
a first indicator for indicating an angular orientation when viewed along the longitudinal axis of the shaft, the first indicator being movable by the user to a selected angular orientation, and
a second indicator for indicating another angular orientation when viewed along the longitudinal axis of the shaft.

49. The needle of claim 48, wherein:

the first and second indicators are moved to positions to provide angular information regarding a tissue area to be removed from the breast.

50. The needle of claim 48, wherein:

the first indicator is coupled to an anchoring element, the anchoring element being displaced angularly with respect to the longitudinal axis when the first indicator is moved by the user.

51. The needle of claim 50, wherein:

the anchoring element is a thin, elongate element which pierces the breast tissue.

52. The needle of claim 50, wherein:

the anchoring element is a wire.

53. The needle of claim 52, wherein:

the wire extending through a slot in the shaft.

54. A method of excising breast tissue, comprising the steps of:

providing a guide element and a cutting device, the cutting device having a deployable cutting element mounted on a shaft, the cutting device also having a tissue collection element;

introducing the guide element into a patient's breast;

advancing the cutting device into the patient's breast, the cutting device being slidably coupled to the guide element so that the guide element guides the cutting device as the cutting device is advanced into the patient's breast;

deploying a cutting element on the cutting device after the advancing step, the cutting element moving from a collapsed position to an expanded position, the cutting element bowing outwardly from the shaft when being deployed;

rotating the shaft so that the cutting element severs breast tissue, the severed breast tissue entering the tissue collection element which trails the cutting element as the cutting element moves through the breast tissue when the shaft is rotated; and removing the breast tissue which has been severed by the cutting element and is contained within the tissue collection element.

55. The method of claim 54, wherein:

the providing step is carried out with the guide element being a needle; and the advancing step being carried out with the cutting device being advanced over the needle.

56. The method of claim 54, wherein:

the rotating step is carried out with the shaft rotating less than 180 degrees relative to the guide element.

57. The method of claim 54, wherein:

the providing step is carried out with the guide element having an indicator for a desired depth of penetration of the cutting device during the advancing step.

58. The method of claim 54, wherein:

the removing step is carried out with the tissue collection element surrounding and isolating the severed tissue from the surrounding tissue.

* * * * *

UNITED STATES PATENT AND TRADEMARK OFFICE
CERTIFICATE OF CORRECTION

PATENT NO. : 6,936,014 B2
DATED : August 30, 2005
INVENTOR(S) : Vetter et al.

It is certified that error appears in the above-identified patent and that said Letters Patent is hereby corrected as shown below:

Column 7,
Line 36, replace "ant" with -- out --.

Column 9,
Line 57, replace "on" with -- one --.
Line 65, replace "stops" with -- steps --.

Column 10,
Line 28, replace "on" with -- one --.

Signed and Sealed this

First Day of November, 2005

JON W. DUDAS
*Director of the United States Patent and Trademark Office*